United States Patent [19]
Mehdian

[11] Patent Number: 5,217,497
[45] Date of Patent: Jun. 8, 1993

[54] APPARATUS FOR USE IN THE TREATMENT OF SPINAL DISORDERS

[76] Inventor: Seyed M. H. Mehdian, Princess Elizabeth Orthopaedic Hospital, Wonford Road, Exeter, EX2 4UE, Devon, England

[21] Appl. No.: 725,588

[22] Filed: Jul. 3, 1991

[30] Foreign Application Priority Data

Jul. 4, 1990 [GB] United Kingdom ............... 9014817

[51] Int. Cl.⁵ .......................... A61F 2/44; A61B 17/00
[52] U.S. Cl. ........................................ 623/17; 606/61; 606/69; 606/80
[58] Field of Search ...................... 623/17; 606/61, 69, 606/80

[56] References Cited

U.S. PATENT DOCUMENTS

| | | | |
|---|---|---|---|
| 3,604,487 | 9/1971 | Gilbert | 145/50 D |
| 3,997,138 | 12/1976 | Crock et al. | 606/61 |
| 4,782,833 | 11/1988 | Einhorn et al. | 606/80 |
| 5,005,562 | 4/1991 | Cotrel | 128/69 |

FOREIGN PATENT DOCUMENTS

| | | |
|---|---|---|
| 0151892 | 11/1984 | European Pat. Off. |
| 2642643 | 2/1989 | European Pat. Off. |
| 0346521 | 12/1989 | European Pat. Off. |
| 0348272 | 12/1989 | European Pat. Off. |
| 3916198 | 11/1990 | Fed. Rep. of Germany |
| 2624720 | 6/1989 | France |
| 2173104 | 10/1986 | United Kingdom |
| 2223406 | 4/1990 | United Kingdom |

Primary Examiner—Randall L. Green
Assistant Examiner—Debra S. Brittingham
Attorney, Agent, or Firm—Marshall, O'Toole, Gerstein, Murray, Borun

[57] ABSTRACT

An implant (10) for use in fixing one segment of a spinal column to another segment thereof by means of at least one rod member, comprises a screw member (11) for insertion in the pedicle of a segment of a spinal column and having an enlarged diameter head (13) with an open ended transverse slot (16) to receive a fixing rod member (20), and clamp means having a screw threaded connection with the head (13) of the screw member (11) and having a clamping portion fitting around the outside of the head (13) of the screw member (11) for engaging a fixing rod member (20) inserted in the transverse slot (16) of the screw member (11) and clamping it therein. The clamp means comprises a collar (14) around a reduced diameter portion (19) of the head (13) and a clamping screw (15) having a threaded shank (18) inserted in a threaded counterbore (17) in the head (13) and having a flanged head (22) for engagement with the collar (14). The axial length of the shank (18) is less than the axial length of the collar (14) whereby a rod member (20) can be clamped by the collar (14) without being engaged by the shank (18). Ancillary instruments for use with the implant system include a center punch (40) for locating a hole to be drilled in a pedicle for insertion of a screw member (11), and a screw driver (50) for holding and inserting a screw member (11) into a drilled hole in a pedicle.

12 Claims, 5 Drawing Sheets

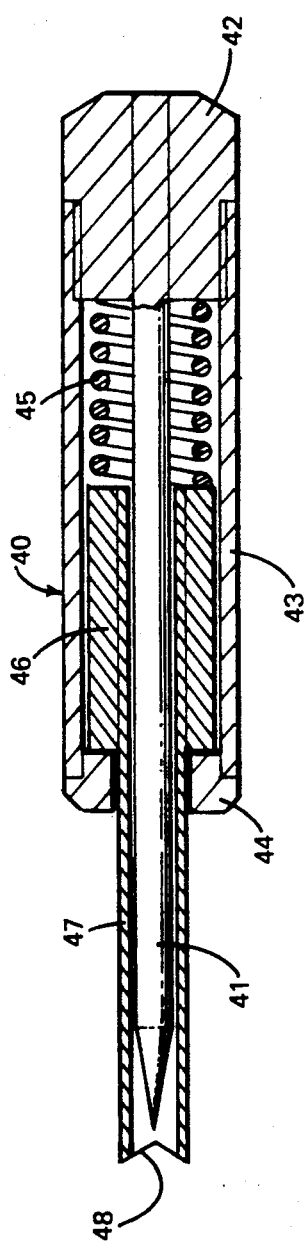
FIG. 8
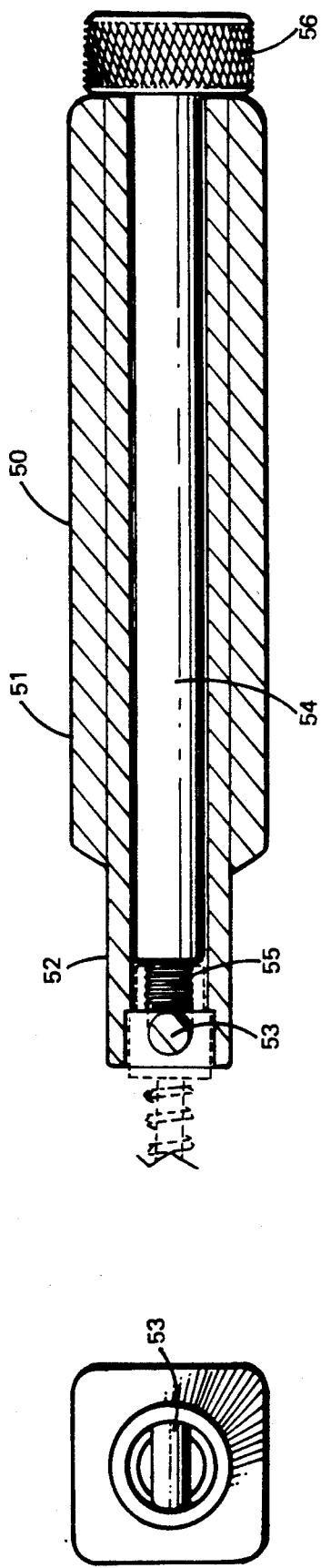
FIG. 10
FIG. 9

APPARATUS FOR USE IN THE TREATMENT OF SPINAL DISORDERS

FIELD OF INVENTION

The present invention relates to apparatus for use in the treatment of spinal disorders.

BACKGROUND OF THE INVENTION AND PRIOR ART

In certain methods of treatment of spinal disorders it is desirable to substantially immobilise selected segments of the spinal column against movement relative to one another. For example, one implant system has involved the use of screws, nuts and plates, the screws being inserted in pedicles of selected segments of a spinal column and the plates attached to the screws by means of nuts. Such a system has a number of disadvantages amongst which are difficulties experienced in bending the plate or plates to the required curvature to fit. In another system plates are placed in position first and are then secured by screws and there is considerable risk of breakage of the screws as a result of movement. In yet another system screw threaded rods are used instead of plates or smooth rods and are fixed to slotted pedicle screws by nuts with one nut at each side of each screw, but considerable difficulty is experienced in fixing the rods in the pedicle screws by the nuts as a consequence of the contour of the lumbar spine. In another implant system, slot headed screws have been used in cooperation with rods clamped in the slots of the screws by securing screws; the clamping of the rods has not always been satisfactory and the process of screwing the securing screws into the heads of the slot headed screws has created a substantial risk of splitting the slotted heads o the screws and also has made it extremely difficult to maintain a desired degree of tightness of clamping since the act of tightening one securing screw creates the risk of loosening of an adjacent securing screw.

SUMMARY OF THE INVENTION

An object of the present invention is to provide an implant system for internal fixation which is relatively simple to use, is relatively easy to manufacture, and which is not bulky.

According to the present invention, an implant system for use in fixing one segment of a spinal column relatively to another segment thereof by means of at least one fixing rod member comprises a screw member for insertion in a pedicle of a segment of a spinal column and having an enlarged diameter head with an open-ended transverse slot to receive a fixing rod member, and clamping means having a screw-threaded connection with the head of the screw member and having a clamping portion fitting around the outside of the head of the screw member for engaging a fixing rod member inserted in the transverse slot in the head of the screw member and clamping it therein.

Preferably the screw-threaded connection between the head of the screw member and the clamping means comprises an internally screw-threaded counterbore in the head of the screw member and an externally screw-threaded shank in the clamp means.

Whilst the clamping portion can comprise a skirt concentric with the shank of a clamping means, it is preferred that the clamp means comprises a collar which can be slipped over the outside of the head of the screw member to engage a fixing rod member inserted in the transverse slot in the head of the screw member and serve as said clamping portion, and a clamping screw having a screw-threaded shank for insertion into the screw-threaded bore in the head of the screw member and a flanged head for engagement with the collar.

Preferably the axial length of the shank of the clamping screw is less than the axial length of the collar whereby a rod member can be clamped in the transverse slot by the collar without being engaged by the end of the shank of the clamping screw.

Preferably, the head of the screw member has a reduced diameter portion adjoining the open end of the transverse slot and counterbore over which the collar is slipped. When the head of the screw member, the collar and the flanged head of the clamping screw have substantially the same external diameter, a generally smooth external surface can be provided, which can be enhanced by providing a hexagonal socket in the flanged head of the clamping screw for engagement with a hexagonal ended driver or key. The hexagonal socket can be screw threaded and receive a further locking screw to engage the rod member and provide additional clamping.

Whilst in a preferred embodiment an implant system comprises a screw member for insertion in the pedicle of a segment of a spinal column, a collar to be slipped over the outside of the head of the screw member and a separate clamping screw for insertion in the head of the screw member, it is possible for the collar and clamping screw to be combined in the form of a skirted screw-in cap; moreover it is also possible for the collar and clamping screw to be combined in the form of a skirted screw-on cap.

When using an implant system embodying the present invention for fixing one or more segments of a spinal column relative to one another, a hole is drilled first into a pedicle of a selected segment of the spinal column and the screw member is screwed therein. A similar procedure is followed in other segments and when all the desired screw members have been inserted, those at each side of the spinal column are aligned with one another so far as the transverse slots are concerned and a rod member, shaped as desired if necessary, is inserted in the transverse slots of the inserted screw members at one side of the spine. A collar is slipped over the reduced diameter portion of the head of each inserted screw member, and then clamping screws are inserted into the threaded counterbores and tightened to cause the collars to apply the necessary clamping pressure to clamp the rod member in the slots.

In order that an implant system embodying the present invention can be used to best advantage, ancillary instruments are desirable for use therewith. Such instruments comprise for example a centre punch for locating a hole to be drilled in a pedicle of a segment of a spinal column, and a locking screw driver for screwing an implant into a drilled hole in a segment. A further aspect of the present invention lies in such ancillary instruments as herein described and useful for utilising an implant system embodying the present invention to best advantage.

BRIEF DESCRIPTION OF THE DRAWINGS

The invention will be further described by way of example with reference to the accompanying drawings, in which:

FIG. 8 is a longitudinal section of a centre punch suitable for use with an implant system embodying the present invention;

FIG. 9 is an end view of a locking screw driver suitable for use for inserting an implant embodying the present invention into a hole drilled in a pedicle of a segment of a spinal column;

FIG. 10 is a longitudinal section of the screw driver of FIG. 9 showing diagrammatically an implant secured therein;

DETAILED DESCRIPTION OF THE PREFERRED EMBODIMENTS

Figure 1:
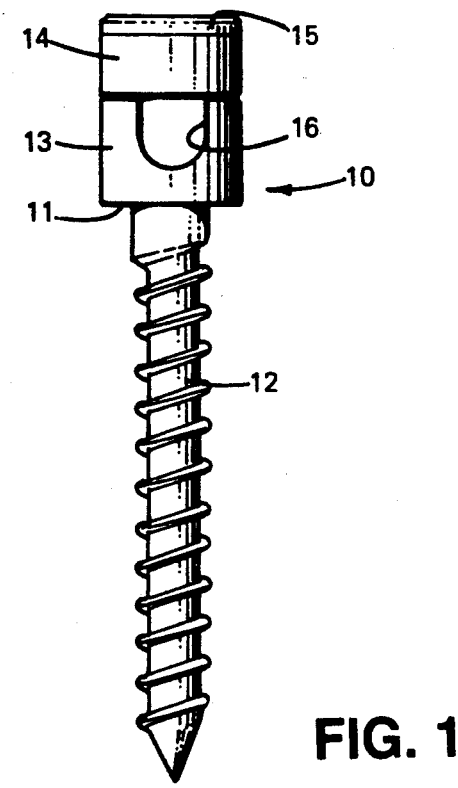
FIG. 1 is a side view of an implant or insert of an implant system according to a preferred embodiment of the present invention.
Figure 2:
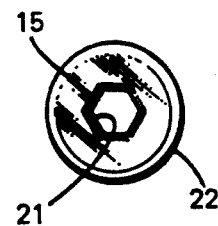
FIG. 2 is an end view of the implant of FIG. 1.

Referring initially to FIGS. 1 and 2, an implant or insert 10 for screwing into a pedicle of a segment of a spinal column comprises a screw member 11 having a screw-threaded shank 12 and a larger diameter head 13, a collar 14 slipped onto the outside of the head, and a clamping screw 15. A transversely extending slot 16 is formed in the head 13 and a hexagonal socket 21 is formed in the clamping screw 15.

Figure 3:
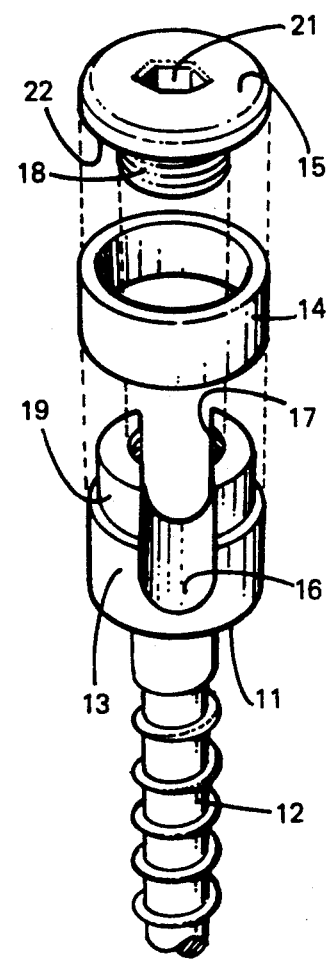
FIG. 3 is an exploded view of the parts of the implant of FIG. 1.
Figure 4:
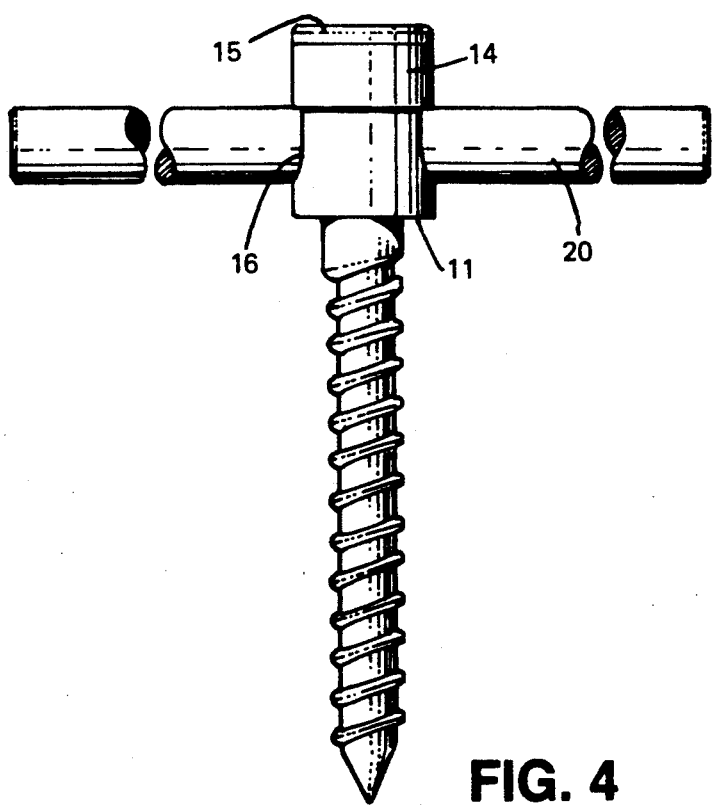
FIG. 4 is a diagrammatic illustration of a rod member clamped in an implant of FIG. 1.

The screw member 11, collar 14 and clamping screw 15 are shown in greater detail diagrammatically in FIG. 3. The slot 16 in the head 13 of the screw member is open ended and has a radiused bottom and the width of the slot and the radius bottom of the slot are selected according to the diameter of a rod member to be received therein. The open end of the slot 16 is counterbored and screw-threaded as at 17 to receive a correspondingly screw-threaded shank 18 of the clamping screw 15. Adjoining the open end of the slot 16 the head 13 of the screw member has a reduced diameter portion 19 onto which the collar 14 can be slipped. In use, the clamping screw 15 and the collar 14 are removed from the head of a screw member 11 which is then screwed into a pedicle of a segment of a spinal column as will be hereinafter described; subsequently a rod member such as 20 is laid in the slot as illustrated in FIG. 4, the collar 14 is slipped over the outside of the head of the screw member, and the clamping screw 15 is screwed into the head to cause its flanged head 22 to apply clamping pressure to the rod member 20 through the collar 14.

Figure 5:
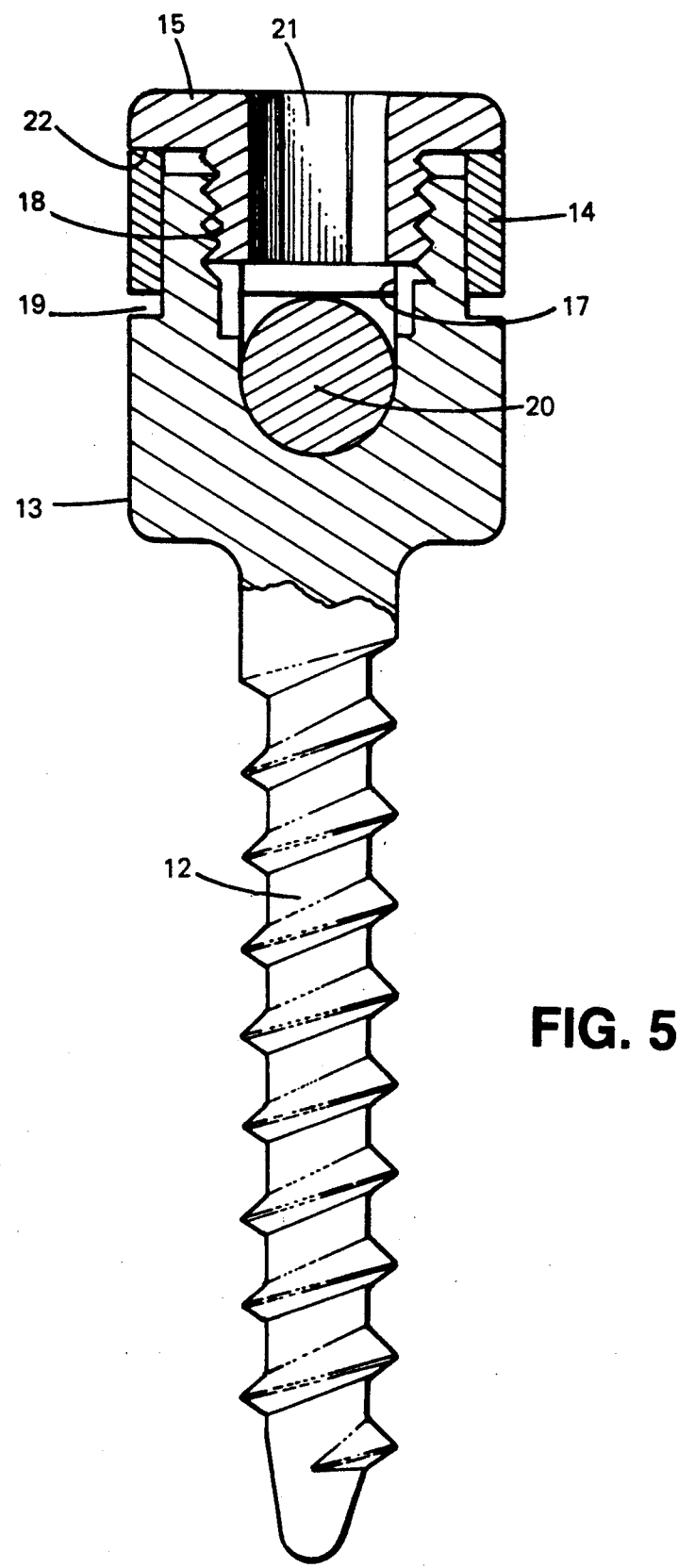
FIG. 5 is a sectional view to an enlarged scale of a rod member clamped in an implant.

It is preferable for the clamping pressure to be applied to the rod member 20 by the collar 14 and not by the shank 18 of the clamping screw 15. This can readily be achieved as illustrated in FIG. 5 by making the axial length of the shank 18 of the clamping screw 15 less than the axial length of the collar 14.

It is very desirable that the external surface of the screw member, the collar and clamping screw should be smooth and free of roughness, and it is advantageous if the head 13, the collar 14 and the flanged head of the clamping screw have substantially the same diameter. Likewise it is desirable that wherever possible corners should be rounded and that sharp edges should be avoided.

It is believed that the advantages of an implant system embodying the present invention can best be understood by description of one manner in which such an implant system can be used in the treatment of spinal disorders since a number of ancillary instruments enable the implants to be used more beneficially.

Figure 7:
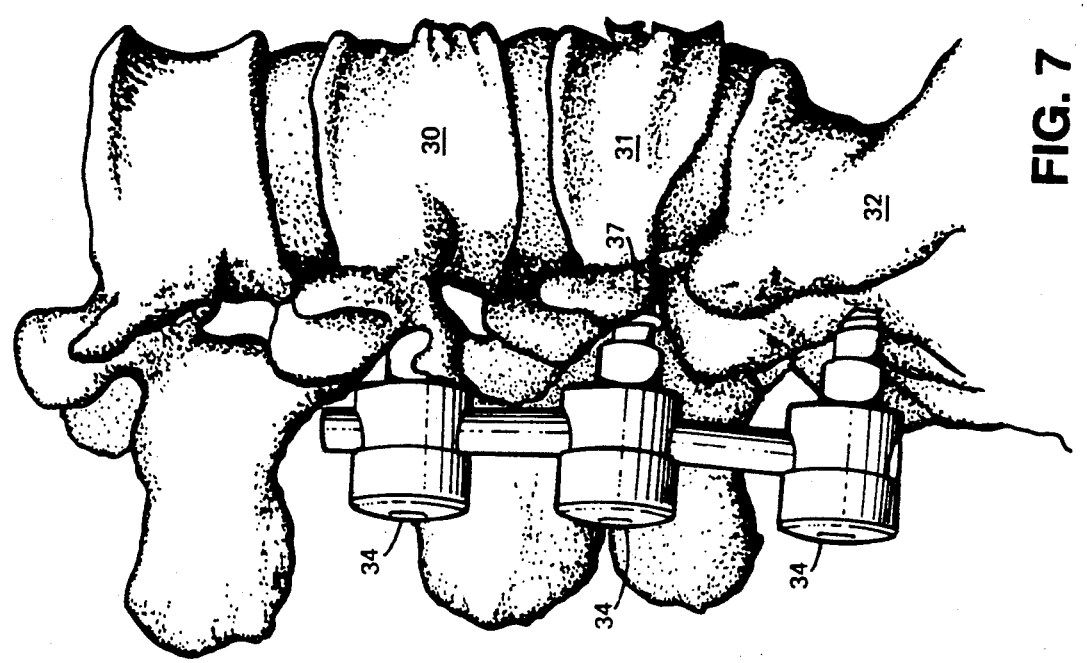
FIG. 7 is a side illustration of FIG. 6.
Figure 6:
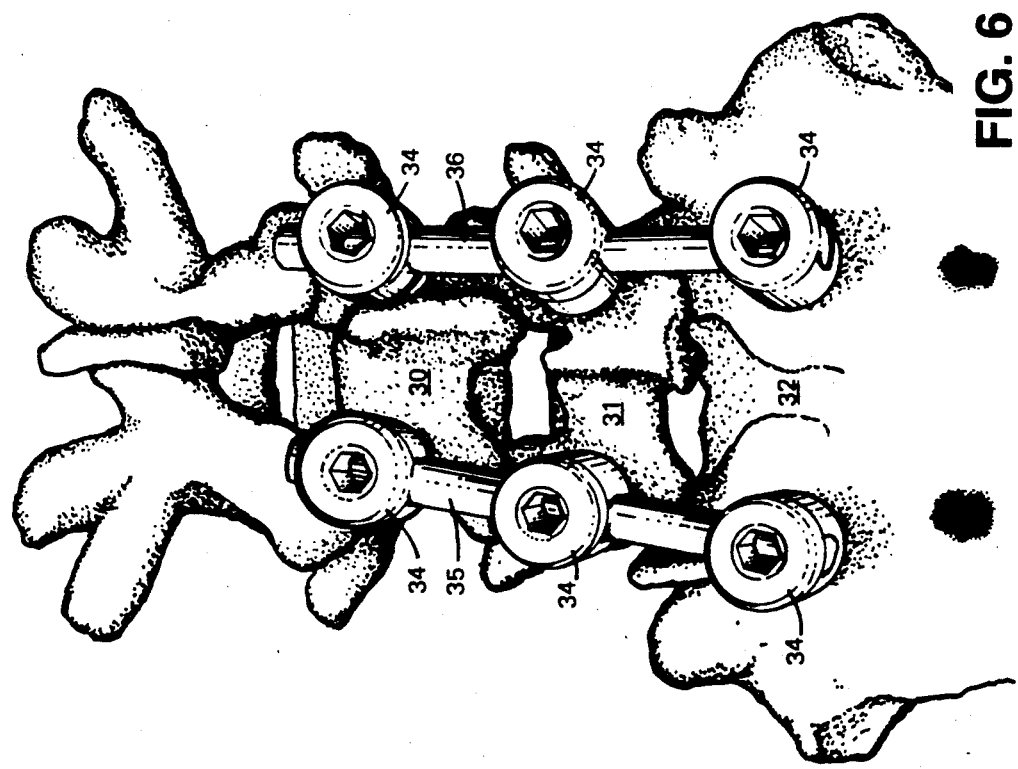
FIG. 6 is a diagrammatic rear elevation of part of a spinal column in which selected segments of the spinal column have been fixed relatively to one another by implants and rod members.

Referring now to FIGS. 6 and 7 let it be supposed that it is desired to fix segments 30 and 31 of a spinal column relative to one another and relatively to sacrum 32 by means of six implants or inserts 34 and two rod members 35, 36. First the collars and clamping screws are removed from the heads of the screw members. Suitable diameter holes are drilled into the pedicles such as 37 of each of the segments. Since it is important that these holes should be drilled in the appropriate places, it is convenient to employ a centre punch such as that illustrated diagrammatically in FIG. 8 to locate the centre of each hole to be drilled. Referring now to FIG. 8, a suitable centre punch 40 comprises a pointed punch member 41 secured to an abutment 42 attached to one end of a tubular handle 43 having at its other end a closure member 44. Surrounding the punch 41 within the tubular handle 43 is a spring member 45 acting between the abutment member 42 and an annular member 46 within the tubular handle 43 and from which extends a tube member 47 surrounding the punch 41. The outer end of the tube member 47 is shaped as at 48 to enable it to be located in a desired position for example straddling a ridge at the rear of a pedicle of a segment of a spinal column. In use, the tubular member is appropriately located against a segment of a spinal column, and pressure is exerted on the anvil 42 to bring the centre punch member 41 into contact with the spinal column, whereupon one or more blows are applied to the anvil 42 to create in the segment of the spinal column a punch hole for location of a drill. The centre punch 40 can be dismantled for cleaning and sterilisation by unscrewing the anvil 42 from the tubular handle 43.

After the necessary holes have been drilled in the pedicles of the segments of the spinal column, it is necessary to screw into place each of the screw members. For this purpose it is desirable for each screw member to be held securely on a screw driver, and one form of locking screw driver 50 for use with these screw members is illustrated in FIGS. 9 and 10, to which reference will now be made. Screw driver 50 comprises a handle 51 surrounding a tubular member 52 which projects from one end of the handle and has at its open end a transversely extending dowel pin 53 of a diameter compatible with the width of a slot 16 in the head of a screw member. In order that a screw member can be securely held in the screw driver 50 a rod 54 extends inside the tube 52 and has at its end a screw-threaded portion 55 to be received in the screw-threaded counterbore 17 upon relative rotation of an external knob 56 attached to the other end of the rod 54. By means of a screw driver 50 a screw member can be adequately held and thereby accurately located so as to be screwed into the preformed hole in the pedicle of a segment; once the screw member has been screwed in sufficiently far the screw driver 50 can be released by unscrewing the threaded end of the rod 54 out of the screw-threaded counterbore 17 by rotating the knob 56 relatively to the handle 51. The rod 54 can be withdrawn from inside the tube 52 for the purpose of cleaning and sterilisation.

Whilst the locking screw driver illustrated in FIGS. 9 and 10 is particularly suitable for the commencement and the major part of the process of screwing the shank of a screw member into a prepared hole in the pedicle of a segment, a screw driver having a generally T-shaped head can be inserted into the slot in the head of a screw member for the final part of the screwing operation and for orientating the head of each of the screwed in screw members into alignment with the other inserted screw members.

The hexagonal socket 21 is preferably in the form of a throughbore opening in the head 22 of the clamping screw 15 and enables the clamping screw to be placed on and retained on a hexagonal cross section end of a driver to facilitate its insertion in the screw-threaded counterbore 17 and the application of a torque thereto.

The clamping pressure applied to the rod member 20 by the collar 14 as a result of the action of screwing the clamping screw 15 into the counterbore 17 can provide sufficient fixation for most uses, and the clamping action can be improved if the collar 14 is distorted a little under the clamping pressure since the area of contact between the rod member 20 and the collar 14 can thereby be increased. If further clamping is required a locking screw can be provided in the clamping screw 14 and screwed in to engage the rod member 20.

Figure 11:
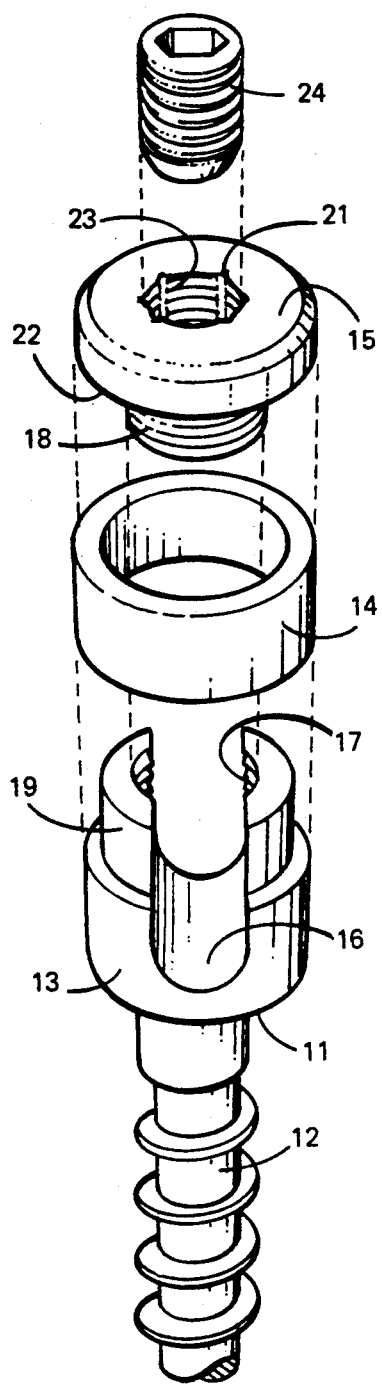
FIG. 11 is an exploded view corresponding to FIG. 3 of the parts of the implant system according to a further embodiment of the invention.
Figure 12:
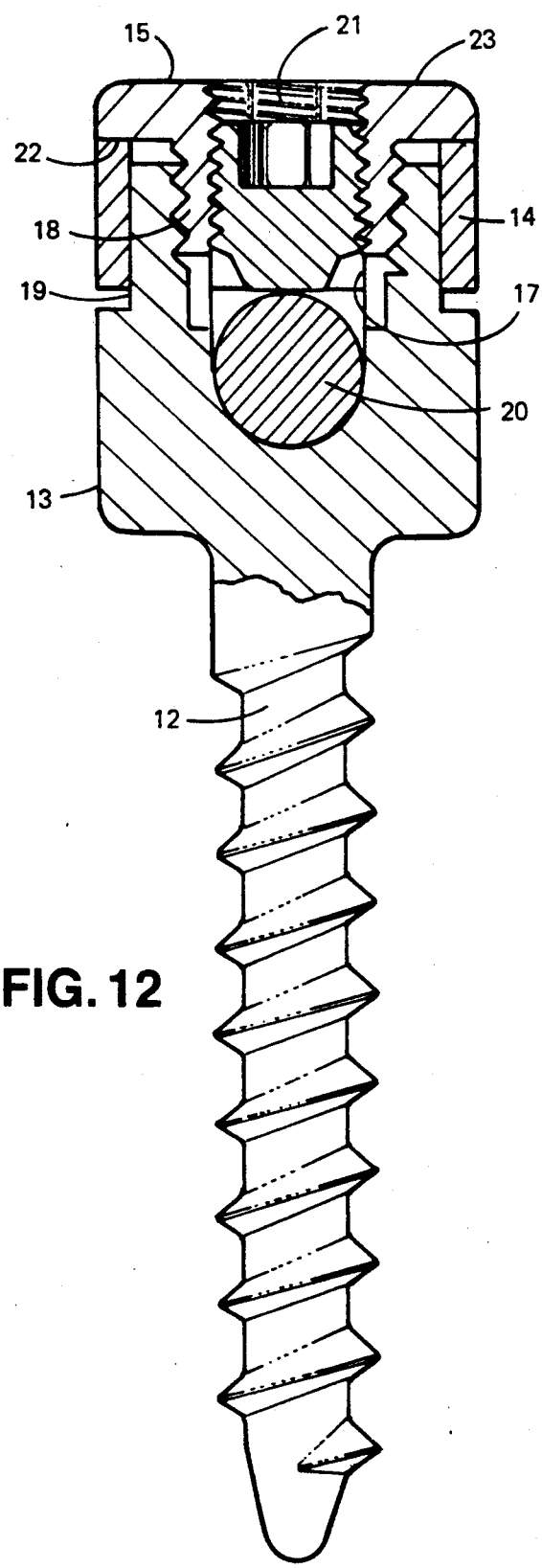
FIG. 12 is a sectional view to an enlarged scale of a rod member clamped in an implant system of FIG. 11.

Such a further locking screw is provided in an implant system according to a further embodiment illustrated in FIGS. 11 and 12 to which reference will now be made. The screw member 11 and collar 14 are the same as in the embodiment of FIGS. 1 to 5, but the hexagonal socket 21 in the clamping screw 15 additionally screw threaded as at 23 to receive further locking screw 24 in the form of a grub screw with a hexagonal socket 24. After the clamping screw 15 has been screwed into the counterbore 17 to apply clamping pressure to the rod member 20 through the collar 14, the locking screw 24 can be screwed into the clamping screw 15 to engage the rod member 20 as illustrated in FIG. 12 and provide secondary clamping action. Preferably the axial length of the locking screw 24 is not greater than the axial length of the clamping screw 15 so that when screwed in to engage the rod member 20, it does not project above the head of the clamping screw 15.

Whilst the diameter and lengths of rod members required are largely determined by the condition of the patient, it is believed that most needs can be met with two sizes of rod member, for example 3/16 inch (4.8 mm) and ¼ inch in diameter (6.4 mm), and with lengths of for example from 4 cm to 14 cm. Again whilst the diameters and lengths of the screw members are largely determined by patient conditions, it is believed that two root diameters of 5 mm for cortical bones and 6 mm for cancellous bone are compatible with rods 3/16 inch (4.8 mm) in diameter, and with root diameters of 6 mm for cortical bones and 7 mm for cancellous bones are compatible with rods ¼ inch (6.4 mm) in diameter. Shank lengths between 30 mm and 50 mm should meet most requirements. With regard to the screw-thread of the shank of a screw member, a V-shaped single start screw-thread with an angle of 60°, flattened crest, a depth in the region of 0.65 to 0.9 mm, and a pitch of 3 mm is suitable for most purposes. Head diameters of 13.7 mm and 12.1 mm, and head heights of 12.6 mm and 11 mm are suitable for screw members for use with ¼ inch (6.4 mm) and 3/16 inch (4.1 mm) diameter rod members respectively. The shank end is preferably conical with an included angle of 40° and rounded. All the screw members, collars and clamping screws, are preferable made of stainless steel as indeed are the rod members.

An implant system embodying the present invention can provide segmental fixation for the control and stabilisation of segments of a spinal column and can be applied to a variety of clinical and pathological conditions affecting the lower thoracic and lumbar spine. The implant system can provide rigid fixation with a low failure rate and can promote graft consolidation for various types of spinal fusions. An advantage of the implant system is that it can permit early mobilisation without prolonged bedrest and bracing, and can thereby ease postoperative nursing care and promote decreased hospital stay.

A further useful feature is the provision of the hexagonal sock et in the head of the clamping screw. Such socket can usefully cooperate with a hexagonal end of a screw driver upon which the clamping screw can be frictionally retained to enable it to be inserted readily into the threaded counterbore in the head of the screw member.

A particular characteristic of an implant system embodying the present invention lies in the fact that the compressive force is applied to the fixing rod by the collar under the influence of pressure applied thereto by the flanged compression screw and that the shank of the compression screw does not engage the rod member. It is believed that it is this characteristic which promotes stability of fixation. The presence of the collar around the outside of the head of the inserted screw member substantially reduces the risk of the head collapsing or becoming fractured as a result of pressure applied to the sides of the slot by the action of screwing in the clamping screw.

I claim:

1. An implant system for use in fixing one segment of a spinal column relative to another segment thereof by means of at least one fixing rod member, said implant system comprising:

a screw member adapted to be inserted in a pedicle of a segment of a spinal column, a collar, and a clamping screw, said screw member having an enlarged diameter head defining an open ended transverse slot adapted to receive a said fixing rod member, said collar being adapted to be slipped over said head whereby one axial end thereof can engage a fixing rod member received in said transverse slot, said head having a screw threaded counterbore leading to said transverse slot for receiving a screw threaded shank of said clamping screw, said clamping screw having a head flange adapted to engage said collar, an axial length of the shank of the clamping screw being less than an axial length of the collar whereby a rod member inserted in said transverse slot can be clamped therein by said collar without said rod member being engaged by the shank of the clamping screw.

2. An implant system as set forth in claim 1 wherein said clamping screw has a hexagonal socket opening into said flanged head for engagement with a hexagonal end of a screw driver or key.

3. An implant system as set forth in claim 2 wherein said hexagonal socket is screw threaded and a further locking screw is screwed therein to engage said rod member in said transverse slot to provide further clamping action.

4. An implant system for use in fixing one segment of a spinal column relative to another segment thereof by means of at least one fixing rod member, said implant system comprising:
   a screw member,
   an external collar, and
   a clamping screw,
   said screw member having a screw threaded shank adapted to be screwed into a pedicle of a segment of a spinal column and a head having an open end of larger diameter than the shank and defining a transverse slot adapted to receive a said fixing rod member for interconnecting said implant system with another implant system in a pedicle of another segment of the spinal column, and having a screw threaded counterbore leading to said transverse slot,
   said screw member also having a portion of reduced external diameter adjoining the open end of said slot and counterbore,
   said external collar being adapted to be received on said reduced external diameter portion of said head of said screw member to engage a said fixing rod member after insertion in said transverse slot,
   said clamping screw having a screw threaded shank adapted to be received in said screw threaded counterbore and having a head flange for engagement with said collar, the clamping screw having a shank portion which has an axial length less than an axial length of the collar whereby the clamping screw when screwed into the counterbore of the head of the screw member can exert clamping pressure on the collar and the collar can exert clamping pressure on a said fixing rod member in said transverse slot of the head of the screw member without an end of the shank portion of the clamping screw engaging the said fixing rod member.

5. An implant system as set forth in claim 4 wherein said clamping screw has a hexagonal socket opening into said flanged head for engagement with a hexagonal end of an ancillary instrument.

6. An implant system as set forth in claim 5 wherein said hexagonal socket is screw threaded and a further locking screw is subsequently received in said socket to engage a said rod member in said transverse slot to provide further clamping action.

7. An implant system for use in fixing one segment of a spinal column relative to another segment thereof by means of at least one fixing rod member when treating spinal disorders, said implant system comprising a screw member for insertion in a pedicle of a segment of a spinal column, and clamp means adapted to cooperate with said screw member, said screw member having an enlarged diameter head defining an open ended transverse slot to receive a fixing rod member, said clamp means comprising a collar and a clamping screw, said collar being configured to fit over the head of the screw member and engaging a fixing rod member inserted in said transverse slot of said head of said screw member, said head of said screw member having a screw threaded counterbore leading to said transverse slot, and said clamping screw having a screw threaded shank adapted to be received in said screw threaded counterbore and having a flanged head adapted to engage said collar when located over the head of the screw member.

8. An implant system as set forth in claim 7 wherein the axial length of the screw threaded shank of the clamping screw is less than the axial length of the collar whereby a rod member can be clamped in said transverse slot by being engaged by said collar without being engaged by the end of the shank of the clamping screw.

9. An implant system as set forth in claim 8 wherein said head of said screw member has a reduced diameter portion adjoining the open end of the transverse slot and counterbore and adapted to receive said collar.

10. An implant system as set forth in claim 9 wherein said head of said screw member, said collar, and said flanged head of said clamping screw have substantially the same external diameter.

11. An implant system as set forth in claim 7 wherein said clamping screw has a hexagonal socket opening into the flanged head thereof for engagement by a hexagonal ended driver or key.

12. An implant system as set forth in claim 11 wherein said hexagonal socket is screw threaded and a further locking screw is subsequently screwed into said socket for engagement with a said rod member in said transverse slot to provide further clamping action.

* * * * *